United States Patent [19]
Collart et al.

[11] Patent Number: 6,153,398
[45] Date of Patent: Nov. 28, 2000

[54] METHOD TO IDENTIFY SPECIFIC INHIBITORS OF IMP DEHYDROGENASE

[75] Inventors: Frank R. Collart, Bolingbrook; Eliezer Huberman, LaGrange, both of Ill.

[73] Assignee: The University of Chicago, Chicago, Ill.

[21] Appl. No.: 08/997,758

[22] Filed: Dec. 24, 1997

[51] Int. Cl.[7] .............................. C12Q 1/32; C12N 9/04; C12N 1/20; C12N 5/00
[52] U.S. Cl. ................... 435/26; 435/190; 435/252.31; 435/252.32; 435/254.4; 435/325
[58] Field of Search .................. 435/26, 190, 252.31, 435/252.32, 254.4, 325

[56] References Cited

U.S. PATENT DOCUMENTS 5,314,813  5/1994  Peterson et al. ..................... 435/172.3

FOREIGN PATENT DOCUMENTS

WO 95/19441  7/1995  WIPO .
WO 90/09448  8/1998  WIPO .

OTHER PUBLICATIONS

Carr, SF et al. (1993). "Characterization of Human Type I and Type II IMP Dehydrogenases." Journal of Biological Chemistry. 268(36): 27286–27290.

Amman, E. et al., Gene, vol. 69, pp. 301–315, 1988.
Kim, B. et al., Proc. Natl. Acad. USA, vol. 92, pp. 684–688, Jan. 1995.
Ashbaugh, C. et al., Gene, vol. 165, pp. 57–60, 1995.
Ashbaugh, C. et al., Genbank, Accession No. U26056, Jul. 1996.

*Primary Examiner*—Ponnathapu Achutamurthy
*Assistant Examiner*—Peter P. Tung
*Attorney, Agent, or Firm*—Barnes & Thornbury; Alice O. Martin

[57] ABSTRACT

This invention relates to methods to identify specific inhibitors of the purine nucleotide synthesis enzyme, IMP dehydrogenase (IMPDH). IMPDH is an essential enzyme found in all free-living organisms from humans to bacteria and is an important therapeutic target. The invention allows the identification of specific inhibitors of any IMPDH enzyme which can be expressed in a functional form in a recombinant host cell. A variety of eukaryotic or prokaryotic host systems commonly used for the expression of recombinant proteins are suitable for the practice of the invention. The methods are amenable to high throughput systems for the screening of inhibitors generated by combinatorial chemistry or other methods such as antisense molecule production. Utilization of exogenous guanosine as a control component of the methods allows for the identification of inhibitors specific for IMPDH rather than other causes of decreased cell proliferation.

13 Claims, 10 Drawing Sheets

Inhibitor Assay

Human IMPDH                Streptoccus IMPDH

Guanosine Effect

Human IMPDH

Human IMPDH
+ Guanosine

```
                  -35                              -10
5'-AACATTGAAATAAACATTTATTTTGTATATGATGAGATAAGTTAGTTTATTGGATA

ACAAACTAACTCAATTAAGATAGTTGATGGATAAACTTGTTCACTTAAATCAAAGG

START     SpeI   EcoRV   STOP         ******* ****
GGGAAATGACAAATGGTCCAAACTGTGATATCTAAAAATCAAAGGGGAAATG

BamHI
GGATCCTCT-3'
```

METHOD TO IDENTIFY SPECIFIC INHIBITORS OF IMP DEHYDROGENASE

The U.S. government may have rights in the present invention based an DOE grant No. KP114,63000/011833 between Argonne National Laboratory and the U.S., Department of Energy.

A portion of the disclosure of this patent document contains material which is subject to copyright protection. The copyright owners have no objection to the facsimile reproduction by any of the patent documents or the patent disclosure, as it appears in the Patent and Trademark Office patent file or records, but otherwise reserves all copyright rights whatsoever.

BACKGROUND OF THE INVENTION

This invention includes recombinant genetic methods to identify specific inhibitors of the purine nucleotide synthesis enzyme, inocsine 5'-monophosphate- dehydrogonase (IMPDH); an enzyme with favorable therapeutic potential in a variety of clinical settings.

Developments in combinatorial chemistry allow the rapid and economical synthesis of hundreds to thousands of discrete compounds. These compounds are typically arrayed in moderate-sized libraries of small organic molecules designed for efficient screening. Combinatorial methods, can be used to generate unbiased libraries suitable for the identification of novel inhibitors. In addition, smaller, less diverse libraries can be generated that are descended from a single parent compound with a previously determined biological activity. In either case, the lack of efficient screening systems to specifically target therapeutically relevant biological molecules produced by combinational chemistry such as inhibitors of important enzymes hampers the optimal use of these resources.

Inhibitors of the enzyme IMPDH (EC 1. 1. 1.205) which catalyzes the formation of xanthine monophosphate (XMP) from inosine monophosphate (IMP), are sought -for clinical use. In the purine de novo synthetic pathway, IMPDH is positioned at the branch point in the synthesis of adenine and guanine nucleotides and is, thus, the rate-limiting enzyme of guanine nucleotide biosynthesis. The guanine nucleotide products of the purine de novo pathway are essential precursors for DNA and RNA biosynthesis, Guanine nucleotides are also an important component of vital cellular processes such as glycosylation, signal transduction, and regulation of metabolic pathways. Because of these essential functions involving the activity of IMPDH, all free living organisms contain the necessary genetic information to produce the IMPDH enzyme. At the present time, IMPDH coding regions have been identified for greater than 25 different species with representatives from the eukaryotic, prokaryotic, and archaeal domains.

Because IMPDH is essential in providing the necessary precursors for DNA and RNA biosynthesis, normal tissues that exhibit increased cell proliferation generally exhibit increased IMPDH activity. Similarly, increased cell proliferation is accompanied by elevated enzyme activity in certain rat hepatomas with varied growth rates. These hepatomas manifest IMPDH activities that are disproportionately higher than those of normal tissues, suggesting that IMPDH is associated with cell proliferation and may be linked to either malignant cell transformation or tumor progression. Conversely, inhibiting IMPDH activity should restrict cell proliferation and induce toxicity or cell differentiation.

The essential nature of IMPDH is also reflected in the diverse applications of IMPDH inhibitors in the areas of cancer chemotherapy, viral infections, immunosuppression, and autoimmune diseases. Several IMPDH inhibitors are being evaluated for their utility as antineoplastic agents. One of these, tiazofurin, has undergone Phase-I/II studies to assess its efficacy against end stage leukemia in adult patients (Jayaram et al., 1992) and is moderately effective in inducing clinical remissions. Mizoribine and mycophenolate mofetil are both inhibitors of mammalian IMPDH useful for immunosuppression following organ transplantation (Halloran et al., 1996-1 Hughes et al., 1996; Allison et al., 1996). The immunosuppressive effects of IMPDH inhibitors would be useful in the treatment of chronic inflammatory diseases such as arthritis, diabetes or systemic lupus erythromatosis.

Another IMPDH inhibitor, ribavirin, is an antiviral agent used to treat respiratory syncytial virus (RSV) infections in pediatric patients (Smith et al., 1991) and for the treatment of AIDS (Japour et al., 1996).

These reports demonstrate the therapeutic value IMPDH inhibitors in a variety of clinical settings. The rapid accumulation of sequence information from various organisms will provide new IMPDH enzymes as potential therapeutic targets. Although there are several effective inhibitors of mammalian IMPDH enzymes, the utility of IMPDH inhibitors as antimicrobial, antifungal or antiparasitic therapeutic agents has not been widely investigated. These applications are important in view of the rapid spread of antibiotic, antifungal, and antiprotozoal resistance (Gillespie, 1997; Klepser 1997). The emergence of opportunistic pathogens, especially in the immunocompromised host, and the widespread use of antibiotics have resulted in serious problems in treating infectious diseases.

Several effective inhibitors of human IMPDH such as mycophenolic acid (MPA) or ribavirin have been identified by nonsystematic methods. Such inhibitors of the human enzyme already have a demonstrated utility in several therapeutic modalities (Table 1). A method to identify new inhibitors of human IMPDH with improved selectivity or bioavailability would enhance the clinical utility of these therapeutic agents. In addition, investigation of the clinical or veterinary utility of IMPDH inhibitors as antimicrobial, antifungal or. antiprotozoal agents would be facilitated by a rapid screening assay. These applications are important in view of the rapid spread of resistance to antimicrobial drugs. The emergence of opportunistic pathogens, especially in immunocompromised hosts, and the widespread use of antibiotics have resulted in serious problems in treating infectious diseases. In view of the need for new antimicrobial agents and the promising potential of IMPDH as a therapeutic target, new methods to efficiently identify IMPDH inhibitors would greatly expedite/enhance the clinical or veterinary applications of such agents.

TABLE 1

Clinically Useful Inhibitors of IMPDH

| Inhibitor | Clinical Application | Publications |
| --- | --- | --- |
| Tiazofurin | Cancer therapy | Jayaram et al., 1992 |
| Mizoribine (Bredinin) | Immunosuppression | Halloran et al., 1996 |
| Mycophenolate mofetil | Immunosuppression | Allison et al., 1996 |
| Ribavirin | Antiviral therapy | Smith et al., 1991 |
| Ribavirin | AIDS therapy | Japour et al., 1996 |

There are fundamental differences in sensitivity to inhibitors and in kinetic parameters among the various IMPDH enzymes from eukaryotic, prokaryotic, and archaeal sources. Information in Table 2 was compiled from unpublished results of the inventors and the data in Hagen et al., 1995. Therefore, a large number of candidate inhibitors should be screened to identify the most effective one for each application. However, there is not a procedure to systematically screen the various chemical agents for utility as IMPDH inhibitors. Therefore methods are needed for identifying new specific IMPDH inhibitors

TABLE 2

Comparison of IMP Dehydrogonase Sequences from Eukaryotic, Prokaryotic and Archaeal Sources.

| Characteristic | Human | Mycobactefium tuberculosis | Pyrococcus Furiosus |
|---|---|---|---|
| Molecular Weight(KDa) | 56 | 54.7 | 52.9 |
| Isoelectric Point(cal) | 7.1 | 6.1 | 5.9 |
| IMP-$K_m$(:M) | 20 | 50 | — |
| AND-$K_m$(:M) | 35 | 900 | 50 |
| MPA-$K_j$(nM) | 20 | No inhibition | Slight inhibition |

IMPDH isolated from bacterial sources has been determined to vary widely with respect to allosteric properties, size, and subunit composition. IMPDH isolated from *E. coli* has been purified and characterized as a tetramer of identical subunits. Unlike mammalian enzymes, the *E. coli* IMPDH is reported to be insensitive to the inhibitory effect of the mammalian inhibitor, mycophenolic acid. In *E. coli*, IMPDH has been determined to be the product of the guaB locus. The sequence of the guaB structural gene and surrounding DNA has been determined to span 1.533 Kb and to code for an IMPDH subunit of 511 amino acids with a calculated molecular mass of 54,512.

The *Bacillus subtilis* IMPDH gene has been cloned and, upon reintroduction into a *B. subtilis* strain that overproduced inosine resulted in an increased production of guanosine, accompanied by a decreased accumulation of inosine. The IMPDH gene was localized on a 6.5-Kb insert and further localized to a Hind III-partially digested 2.9-Kb fragment. However, the gene was not reported to have been isolated and no information was provided with respect to the DNA sequence of the gene.

In summary, no general, efficient screening system for IMPDH inhibitors is available. Development of such an assay would enhance and accelerate the discovery of therapeutically useful inhibitors.

SUMMARY OF THE INVENTION

The present invention relates to novel and efficient methods to identify specific inhibitors of IMPDH using recombinant genetics. The methods include a prokaryotic, eukaryotic or archaeal host organism which is an auxotroph for IMPDH; a recombinant DNA vector system transfected into, or used to transform, said organism to produce a recombinant host organism which is capable of producing a functional IMPDH enzyme; suitable selection criteria to assess the effect of various chemicals/compounds on the growth of the recombinant host organism; and utilization of exogenecusly added guanosine/guanine to validate the degree of specificity for inhibition of IMPDH.

A suitable recombinant auxotrophic strain, the host organism, is preferably prokaryotic (microbial) such as a bacterium. A preferred embodiment uses *E coli* strain H712 as a host organism. Other organisms suitable for the practice of the invention include eukaryotic strains such as yeast, fungal, or insect strains (e.g. Neurospara or Drosophila). IMPDH auxotrophs have been described for representatives of these organisms (Nijkamp and DeHann, 1967; Geer and Wellman, 1980) and such organisms are appropriate for transformation and expression of foreign proteins.

A host organism that is an auxotroph for IMPDH is transformed with a gene encoding exogenous IMPDH. This allows simple direct or differential testing of candidate inhibitors of IMPDH from various species. In vivo culture of the transformed host allows candidate inhibitors to be identified by their ability to inhibit transformed cell proliferation. Controls to confirm that the inhibition is effected through action on IMPDH are prepared by supplementation with guanine nucleotide precursors in the culture media in which the auxotrophic organism is growing, to correct the defect.

The screening system of the present invention has a number of advantages for the identification of specific IMPDH inhibitors:

1. The screening system is amenable to high throughput systems for the screening of inhibitors generated by combinatorial chemistry or by other methods. For example, a preferred embodiment utilizes multiple well microliter plates and an automated system to dispense media and screen compounds. An example of an automated screening procedure designed for use with 96 well microliter plates is in Strong-Gunderson and Palumbo (1994). A screening experiment with a bacterial host using microliter amounts of reagents can be completed in a minimum of several hours.

Other screening permutations include metabolic activation of candidate chemicals as a resource for IMPDH inhibitors. Examples of such inhibitor generating systems include the injection of a recombinant host organism into an animal or culture of a recombinant host organism with a) an artificial system capable of producing putative IMPDH inhibitors; b) cell homogenate(s) (e.g. microsomes); c) cultured cells capable of generating putative inhibitors by cellular synthesis or by metabolic activation of added components. In all such permutations, criteria for evaluating IMPDH inhibition remain the same; i.e. differential host cell growth in the presence and absence of guanosine.

2. The methods of the present invention are useful to screen for inhibitors to IMPDH that are derived from any source for which a DNA coding sequence is available. At the present time, 20–30 different IMPDH coding sequences from the eukaryotic, bacterial and archaeal domains are available in the DNA sequence databases 3. The addition of exogenous guanosine is useful as a method to verify inhibitory chemicals that specifically target IMPDH and to distinguish action of the candidate inhibitors from other causes of host cell inhibition.

4. The methods of the present invention can be used to identify inhibitors capable of differentially inhibiting IMPDH from organisms that are genetically dissimilar.

5. An aspect of the present invention is the identification of specific IMPDH inhibitors, which are useful as the basis for the design of new pharmaceuticals. Inhibitors include antisense molecules and chemicals. New human IMPDH inhibitors are identified for use as chemotherapeutic agents for the treatment of neoplasms and viral diseases and as immunosuppressive agents. Inhibitors of bacterial, fungal, protozoan or viral IMPDH which do not inhibit the human or other mammalian enzymes, may be effective therapeutic agents.

DESCRIPTION OF THE PREFERRED EMBODIMENT

Figure 1:
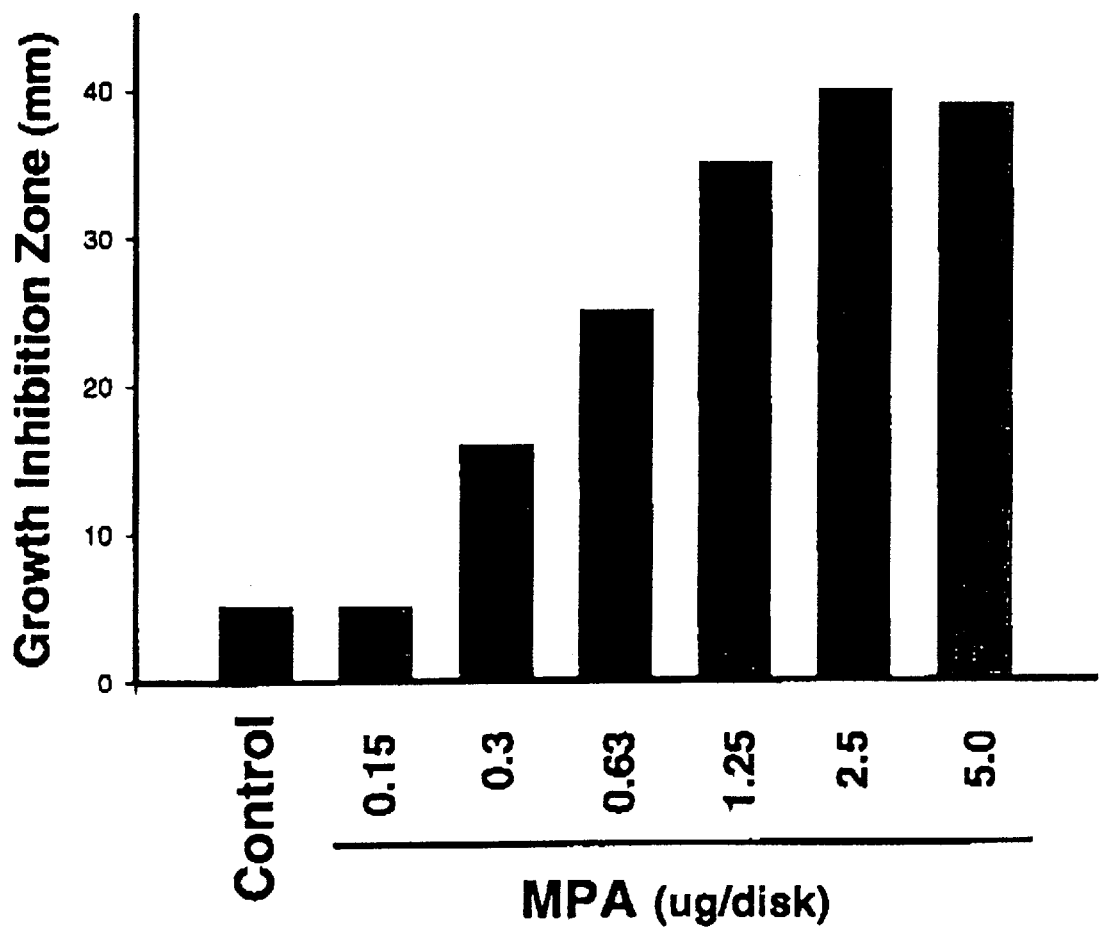
FIG. 1 illustrates dose dependent inhibition of H712 growth.

Recombinant genetic methods of the present invention to screen for specific IMPDH inhibitors utilize a host organism that lacks a functional IMPDH enzyme. Specific inhibitors for a variety of IMPDH enzymes are identified utilizing a variant strain that is a guanine auxotroph. The strain includes in its genetic makeup a defect in the IMPDH gene and does not produce functional IMPDH enzyme. Such a strain requires an exogenous source of guanine or guanosine for growth. A suitable host is a bacterium such as E coli, Bacillus subtilis, and Proteus mirabilis, or a eukaryotic organism such as yeast, fungal or insect strains (e.g. Neurospora or Drosophila). Microbial hosts, such as bacteria are preferred. A preferred, bacterial strain of E. coli is designated H712 and requires the addition of a guanine nucleotide precursor(s) to the culture medium for cell growth. The H712 bacterial strain, originally described by Nijkamp, et al, (1967), was selected to eliminate interference from a resident IMPDH enzyme during the screen for IMPDH inhibitors. It was obtained from the E. coli Genetic Stock Center, Yale University, New Haven, Conn.

To construct a vector, suitable for the practice of the invention, molecular (recombinant) techniques were used to insert the coding regions of the human or Streptococcus pyogenes IMPDH genes into a vector capable of expressing these genes in a host bacteria, e.g. the E. coli H712 bacteria. Bacteria containing this vector system produce the human or S. pyogenes IMPDH protein and no longer require the addition of guancsine to the culture medium for growth. Furthermore, the IMPDH enzymes produced in the E. coli host retain the biochemical and kinetic characteristics of the source (i.e., either human or S. pyogenes).

This invention utilizes a combination of a host organism that is a guaninc auxotroph, a recombinant DNA expression vector, and a screening system to identify specific inhibitors of IMPDH. The recombinant expression vector has the properties of containing a prokaryotic, eukaryotic, or archaeal IMPDH coding sequence or a chimeric enzyme containing coding sequences from various natural or synthetic sources. These coding sequences have the ability to express a functional IMPDH enzyme in the host organism. The IMPDH product of this expression system is the target for a screening protocol to assess the specificity and potency of compounds inhibiting the growth of the host organism. The screening component of the invention takes advantage of several unique characteristics of IMPDH enzymes which are essential for the successful identification of inhibitors and the broad applicability of this invention to IMPDH enzymes from prokaryotic, eukaryotic, and archaeal organisms.

A component of this method includes a prokaryotic, eukaryotic or archaeal host organism which is a guanine auxotroph with the specific characteristic that the organism is defective in the production of a functional IMPDH enzyme. An IMPDH defective organism allows expression of a nonnative recombinant IMPDH enzyme without interference from the host IMPDH enzyme. Guanine auxotrophs with a specific IMPDH defect have been reported for both prokaryotic (Nijkamp and DeHann 1967; Freese et al., 1979) and eukaryotic (Greer and Wellman, 1980) organisms.

General recombinant DNA methods have been described to generate specific auxotrophs via homologous recombination for both prokaryotic (Winans et al., 1985) and eukaryotic (Mortensen et al., 1993) organisms. For the purpose of this invention, an aspect of which is identification of specific inhibitors of IMPDH, a variety of guanine auxotrophs are available and are suitable for incorporation in the screening procedure. Consideration of the eventual therapeutic target are factors such as availability, convenience or suitability for mass screening protocols are factors to consider in the selection of a specific host organism. Specific guidelines for the selection of an appropriate host organism include:

1. a host organism must be a guanine (or a derivative) auxotroph with a low reversion frequency;

2. a host organism must be competent for transformation with the recombinant expression vector;
3. the genome of a host cell must be compatible with the recombinant expression system to allow production of a functional IMPDH enzyme;
4. the selection of a host organism with metabolic pathways similar to those of the therapeutic target organism (e.g. human) with respect to inhibitor activation or modification enhances clinical utility.

Another component of the invention is a recombinant DNA vector system transfected into, or used to transform, the host organism thereby generating a recombinant organism that is capable of producing a functional IMPDH enzyme. The expression vector used in the screening process must be compatible with the host organism. However, a variety of expression systems are available for both prokaryotic and eukaryotic organisms. These include specific expression systems such as the pPOLT7/pBET7 (Conrad et al., 1996) or the pX (Kim et al., 1996) systems or more general expression vector such as pMMB66EH (Fürste et al., 1986) which is suitable for expression in E. coli, Protezus mirabilis, Serratia marcescens, Pseudomonas aeruginosa and other gram negative bacteria. Similarly, there are many vectors suitable for expression in eukaryotic hosts (Roth, 1994). A suitable broad host range vector for the practice of the invention is the plasmid pJF118EH, constructed by Fürste et al., 1986. This expression system uses ampicillin resistance as a selectable marker and permits the regulated expression of foreign coding sequences in an E. coli host. The pJF118EH vector has the properties of inducible expression such that in the absence of an inducer the expression of the cloned foreign is low. Induction of the foreign gene is initiated by the addition of IPTG to the bacterial culture medium. Other similar expression vectors, whether inducible or constitutive, are suitable for obtaining a recombinant host organism expressing a functional IMPDH enzyme.

The combination of an expression system producing functional IMPDH and a guanine auxotroph allows the screening of agents targeting the expressed IMPDH product. The effects of various agents are assessed by their ability to inhibit host cell proliferation. Since IMPDH produces essential precursors for DNA and RNA biosynthesis, inhibition of IMPDH activity reduces the proliferation rate and thus provides an easily quantifiable marker to assess the effects of various agents that may affect the activity of IMPDH.

However, there are chemicals that inhibit host cell proliferation regardless of whether or not the host is expressing a prokaryotic or eukaryatic IMPDH enzyme. To identify agents specifically targeting IMPDH, the inhibitor profile for a particular agent is compared to the same profile obtained when a guanine nuclectide precursor such as guanine or guanosine is added to the culture medium. Guanosine is a preferred agent due to its high solubility in aqueous solutions. These guanine nucleotide precursors are able to circumvent the block on IMPDH activity imposed by IMPDH inhibitors and are used to exclude nonspecific growth inhibitory or toxic compounds. Agents specifically targeting IMPDH exhibit a decreased ability to inhibit cell proliferation in the presence of guanine/guanosine while the growth inhibitory effects of nonspecific or toxic agents are not ameliorated by guanine/guanosine.

This invention utilizes a combination of auxotrophic host organisms and molecular expression techniques to provide a screening system suitable forthe identification of specific inhibitors of IMPDH from a variety of sources. The novelty of the invention resides in the ability of this unique combination of the host organism, vector, and screening system to mimic the phenotype of the recombinant IMPDH enzyme. It is surprising that the expression of a single protein in a background of several thousand host cell proteins would result in a phenotype sensitive to the characteristics of the recombinant protein Although numerous recombinant proteins have been expressed in heterologous systems, there are no guidelines to insure that the protein will not be expressed as inclusion bodies or that the functional characteristics will be maintained. It is unpredictable whether expression will occur. It is even more unlikely that the recombinant protein would be able to replace the function of the host cell protein if the recombinant protein is genetically distinct.

In this invention, the expression of a heterologaus IMPDH enzyme in a bacterial system lacking an endogenous IMPDH enzyme permits the growth of a host bacterium, which is a guanine auxotroph, without the addition of guanine nucleotide precursors. This unusual characteristic of IMPDH enzymes is most likely attributable to functional conservation of IMPDH enzymes that allows IMPDH from multiple sources to be interchanged. Such a functional conservation may have been anticipated for genetically similar organisms, but is unexpected for IMPDH enzymes isolated from eukaryotic or genetically dissimilar organisms (Tiedeman and Smith, 1991; Huete-Perez et al., 1995). These characteristics of the recombinant host organism in conjunction with the use of guanosine as a component of the screening protocol permit the rapid identification of specific inhibitors of IMPDH from a variety of species.

The biological role of IMPDH is the synthesis of precursors essential for nucleic acid biosynthesis. Because of this essential role, all free-living organisms contain the necessary genetic information to produce the enzyme. As a consequence, this invention has a general application to a broad range of organisms. The construction of the recombinant expression system entails the use of sequence information specific for IMPDH. However, the lack of available sequence information for a specific pathogenic organism does not necessarily limit the application of this invention for identification of potential therapeutic agents. The inventors have derived the phylogenetic relationships for IMPDH enzymes from the eukaryotic, prokaryotic, and Archaeal domains of life using information in sequence databases (Collart et al., 1996). The phylogenetic tree derived for IMPDH enzymes is similar to trees developed using other molecular resources. These results suggest application of this screening method to IMPDH from a phylogenetically similar organism will provide therapeutic agents that have utility against a selected pathogenic organism for which an IMPDH coding region is not available, Sequence information specifying coding information for more that 25 IMPDH enzymes representing all three domains of life have been submitted to scientific databases (Table 3) and this number is certain to increase in the near future.

TABLE 3

| Organism | Genbank Database Accession Number | Organism | Genbank Database Accession Number |
| --- | --- | --- | --- |
| *Homo sapiens* | J04208 | *Streptococcus pyogenes* | U26056 |
| *Cricetulus griseus* | J04209 | *Haemophilus influenzae* | U32708 |
| *Mus musculus* | M98333 | *Acinetobacter calcoaceticus* | X66859 |
| *Drosophila melanogaster* | L22608 | *Mycobacterium tuberculosis* | Z77165 |
| *Candida albicans* | U85049 | *Mycobacterium leprae* | U00015 |
| *Saccharomyces cerevisiae* | U21094 | *Helicabacter pylori* | AE000594 |
| *Pneumocystis carinii* | U42442 | *Pyrococcus furiosus* | U08814 |
| *Trypanosoma brucei* | M97794 | *Methanococcus jannaschii* | U67602 |
| *Saccharomyces pombe* | Z97211 | *Borrelia burgdorferi* | U13372 |
| *Leishmania donovani* | M55667 | *Tritrichomonas fbetus* | L18917 |
| *Arabidopsis thaliana* | L34684 | *Ascaris lumbricoides* | M82838 |
| *Bacillus subtilis* | X55669 | *Caenorhabditis elegans* | AF016427 |
| *Escherichia coli* | M10101 | *Synechocystis sp* (PCC6803) | D90910 |
| *Chlorobium vibrioforme* | Z77165 | *Methanobaterium thermoautotrophicum* | AE00803 |

With the present representation of IMPDH coding sequences, application of the method proposed in this invention will be useful for identification of inhibitors of IMPDH enzymes from all the genetic primary lineages of life (e.g. eukaryotic, prokaryotic, Archaeal).

The invention is also useful or the identification of inhibitors of pathogenic organisms which do not contain IMPDH coding regions. Examples of such agents might include various viruses, chlamydia, or other obligate intracellular pathogens. These agents utilize the host organisms' nuclectide pools and often are sensitive to agents that alter the host nucleotide balance. Such observations can account for the effectiveness the IMPDH inhibitor, ribavirin, in the treatment of RSV (Smith et al., 1991) and Hantavirus (Huggins, 1991) infections. These viral agents do not contain the genetic information for IMPDH but rely on host cell synthesis of guanine nucleotides for their metabolic requirements, However, these agents are sensitive to IMPDH inhibitors that alter host cell guanine nucleotide pools and subsequently suppress viral RNA synthesis.

EXAMPLES

The following examples are presented to exemplify not to limit aspects of the invention.

Example 1

Expression of Exogenous IMPDH in a Recombinant Host

To illustrate the utility of the invention, the coding sequence of human and *S. pyogenes* IMPDH were cloned into the pJF118EH expression vector using standard molecular biological techniques (Perbal 1984; Huynh et al., 1985; Maniatis et al., 1982). A source of the DNA, the *Streptoccus pyogenes* bacterium, is available from the ATCC (Accession No. 10090). For the *S. pyogenes* recombinant construct, the coding region of IMPDH was amplified from *Streptococcus pyogenes* genomic DNA (provided by Dr. Michael Boyle, Medical College of Ohio, Toledo, Ohio) using coding region-specific primers and a proof-reading polymerase (Pfu). The amplified fragment was cloned into a pJF118EH expression vector. This broad host range vector, constructed by Fürste, et al. (1986), is suitable for protein expression in a variety of gram negative bacteria. The pJF118EH expression system uses ampicillin resistance as a selectable marker and permits the regulated expression of foreign coding sequences in an appropriate host. In the absence of an inducer, the expression of the cloned foreign gene is extremely low. Induction of foreign gene is initiated in a dose dependent manner by the addition of isopropyl-β-D-thiogalactopyranoside (IPTG) to the bacterial culture medium.

"(a) Construction of an autorepressed broad-host-range expression vector

Plasmid pJF118EH contains the lac repressor gene lacI$^Q$, replacing the large remnant of the tetA gene in plasmid pKK233-3 (FIG. 1). This replacement conserves important properties of the expression vector pKK233-3 and extends the range of the application of the new construct, mainly because transcription can be kept repressed in any *E. coli* strain due to the plasmid-borne lacI$^Q$ gene. Additionally, by removal of most of the tetA gene the recognition sequences for the BamHI and SalI within the polylinker are now unique sites, so that seven sites of the polylinker (EcoRI, SmaI, XmaI, BamHI, SalI, PstI, and HindIII) can be utilized for convenient insertion of fragments." © 1986 Fürste et al.

The expression construct containing the *S. pyogenes* IMPDH coding sequences was used to transform an *E. coli* H712 bacteria using ampicillin resistance as the selectable marker. The H712 bacterium is a guanine auxotroph and requires the addition of a guanine nucleotide precursor(s) to the culture medium for growth. Use of this bacterial strain eliminates interference from the resident IMPDH enzyme during the screen for IMPDH inhibitors. The H712 variant was originally described by Nijkamp et al., (1967) and was obtained through the *E. coli* genetic stock center at Yale University (New Haven, Conn.). Expression of *S. pyogenes* IMPDH was induced by the addition of isopropyl-β-D-thiogalactopyranoside (IPTG) to 0.5 mM.

In a similar manner, coding sequences for human IMPDH were amplified from an expression system for human IMPDH (Hager et al., 1995), cloned into the pJF118EH plasmid, and used to transform H712 bacteria. Four clones containing the human IMPDH coding sequence (designated clones H1, H2, H3 and H4) and two clones containing the *S. pyogenes* IMPDH coding sequence (designated clones S1 and S2) were used for subsequent experiments. Using SDS-PAGE analysis, all of these clones demonstrated expression of the IMPDH protein in the presence of IPTG.

"Expression of IMPDH Protein in *E. coli*. IMPDH I and II were subcloned from pGEM derived vectors into pET24c(+) (Novagen) and expressed in *E. coli* BL-21 (DE3) [8]. Cells were grown at 37° in 10 L of YT+M-9 salts [17] in a New Brunswick fermentor to an $OD_{600}$ of 1–2 and induced with 0.2 to 0.4 mM IPTG. Cells were harvested at 1.5 to 2 hr postinduction, washed with 10 mM Tris-Cl, 1 mM EDTA, 1 mM PMSF, and stored frozen at −70° (approximately 50 g of wet weight cells). cDNA for the coding, sequences of types I and II IMPDH were generated by PCR. PCR primers based on published sequences of IMPDH (16) were designed to incorporate HindIII and NdeI sites at the 5' end and BglII and HindIII sites at the 3' end. The primers used were as follows: type II5': GTA-CAAAGCTTCATATGGCCGACTACCT GATT-AGTGGGGGCACG (SEQ ID NO: 1); and 3': TGA-CAAAGCTTAGATCTTCAGAAAAGCCGCTTCTC ATACGAA (SEQ ID NO: 2); Type I 5': GTA-CAAAGCT TCATATGGCGGACTACCTGAT-CAGCGGCGGCACC (SEQ ID NO: 3); and 3': TGA-CAAAGCTTAGATCTT CAGTACAGCCGCTTTTCGTAAGAG (SEQ ID NO: 4). The PCR products werecloned into PGEM7Zf(+) (Promega, Madison, Wis.) at the HindIII site and excised with NdeI and BgtIII for subcloning into the pET3d *E. coli* expression vector (26). The amplification of the type I cDNA required two rounds of PCR using external primers from the 5' and 3' untranslated regions in the first PCR reaction: 5' primer-CAGATGGATCGCCTTCGCAG (SEQ ID NO: 5); and 3' primer-CTGTGGACCACTCAGTTATG (SEQ ID NO: 6). PCR was performed on cDNA reverse transcribed from RNAs derived from purified human T lymphocytes, the Jurkat T leukemic cell line, and heart, kidney, and placenta. PCR was performed for 30 cycles under the following conditions: 94° C. for 1.25 min, 55° C. for I min, and 72° C. for 3 min. Cloned PCR products were sequenced by the Sanger dideoxy method (27) using the Sequenase 2.0 kit (USB, Cleveland, Ohio). The HLA-B7 class I-specific probe consisted of a 1.4-kb PstI fragment isolated from pHLA-B7 (28)." © 1995 Hager et al.

Other permutations that utilize different prokaryotic and eukaryotic host organisms and compatible expression vectors are also provided for in this invention. The prokaryotic bacterium, *B. subtilis*, is a suitable host organism for identification of specific IMPDH inhibitors. The coding regions of the human and *S. pyogenes* IMPDH are amplified by PCR from genomic DNA using specific primers with flanking BamHI sites. The amplified fragments are ligated into the BamHI site of the pX inducible expression vector (Kim et al., 1996), available from the Bacillus Genetic Stock Center, The Ohio State University, Columbus, Ohio). The plasmids are transformed into *B. subtilis* strain 1A294 (a guanine auxotroph available from the Bacillus Genetic Stock Center) and integrants are selected on LB plates (Maniatis et al., 1982) containing chloramphenicol (5 μm/ml). Expression of the IMPDH enzyme is induced by the addition of 0.8% xylose to the culture medium. The ability of the host organism to produce functional IMPDH is validated by growth of the recombinant host organism on minimal medium containing methionine, tryptophan, and 0.8% xylase.

"2.1. Construction of the integration vector pX

Figure 7:
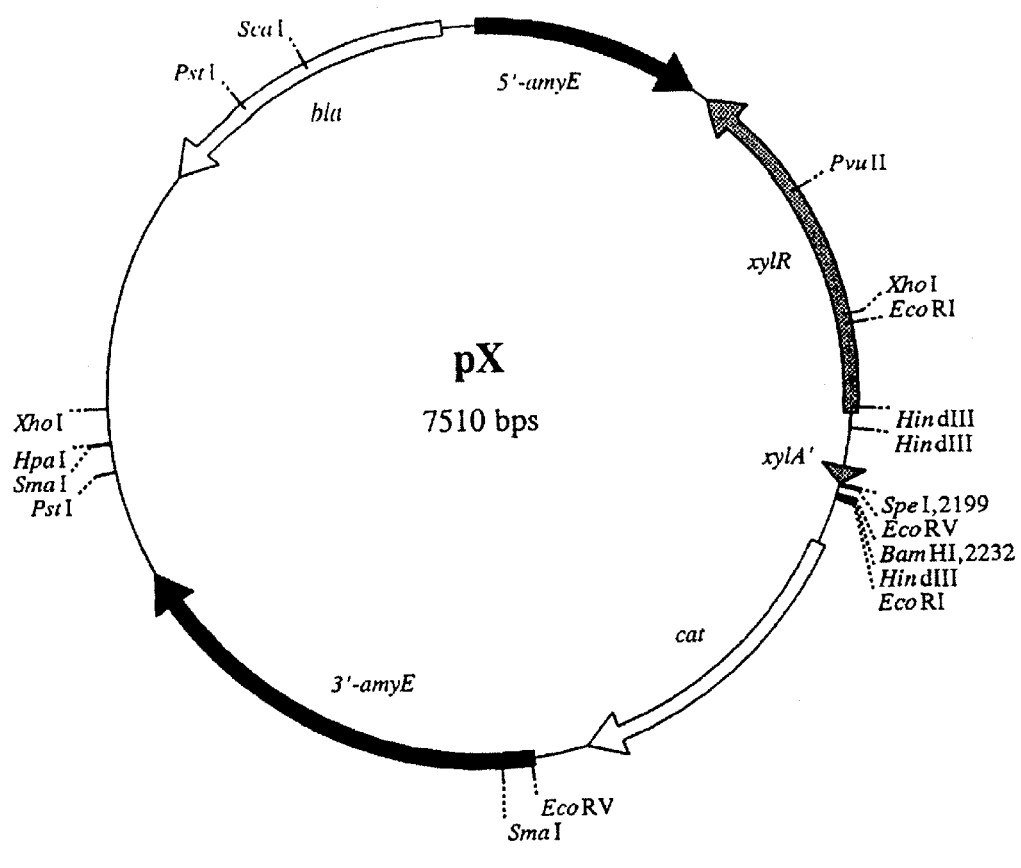
FIG. 7 is a map in the prior art of plasmid pX; "construction of the integration vector pX. To isolate the xlyR-xylA' expression cassette as a BglII fragment, the AflII site downstream of xlyR in pWH1520 (Rygus and Hillen, 1991) was replaced by a BglII site resulting in PLK01, Subsequently, the complete expression cassette was recovered as a 1.7-kb BglII fragment and inserted into the BamnHI+BglII-digested pDG364 (Karmazyn-Campbell et al., 1992) to give pLK02. To remove a second SpeI site situated between bla and amyE-3', pLK02 was cut with BstEII and BglII, the larger fragment was blunt-ended and ligated to yield pLK03. To terminate translation which starts at the xlyA' gene a stop codon was inserted within the xylA reading frame followed by an efficient new RBS. This was accomplished by inserting a 33-bp oligo, flanked by SpeI sand BamHI sites, into the appropriately cleaved pLK03. The physical and genetic map of the resulting pX vector is shown together with the relevant nt sequence between promoter and BamHI site. Indicated are the $\sigma^A$-dependent promoter (boldface letters), the translation start and stop codon of xylA', the synthetic RBS sequence (asterisks above the sequence), and the restriction sites for three different enzymes." © 1996 Kim et al.
Figure 8:
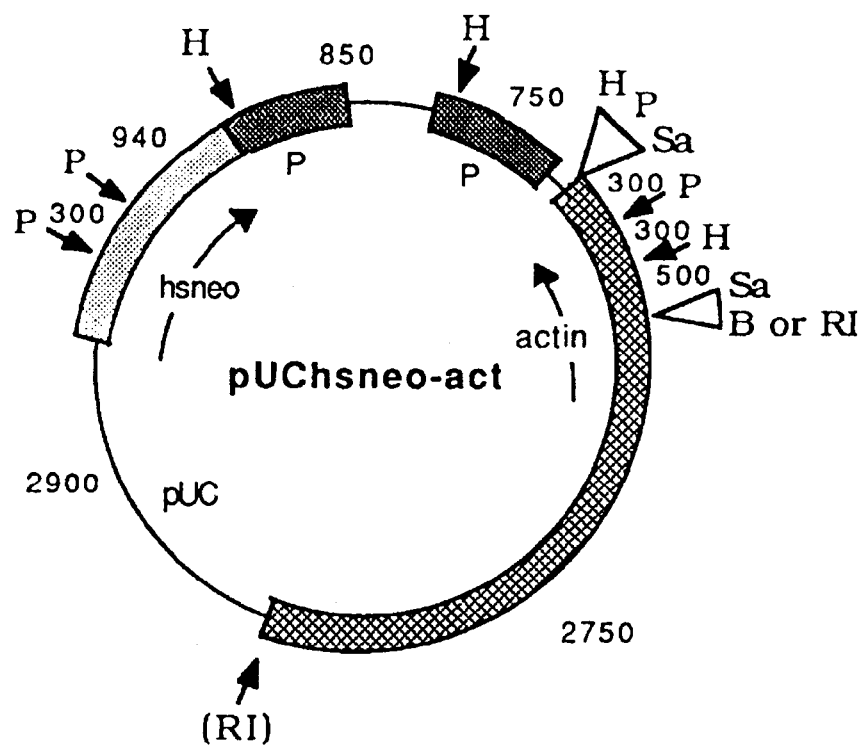
FIG. 8 is a map in the prior art of the pUChsneo-act (Bam) fragment at pUC18. © 1997 Berkowith et al.
Figure 8:
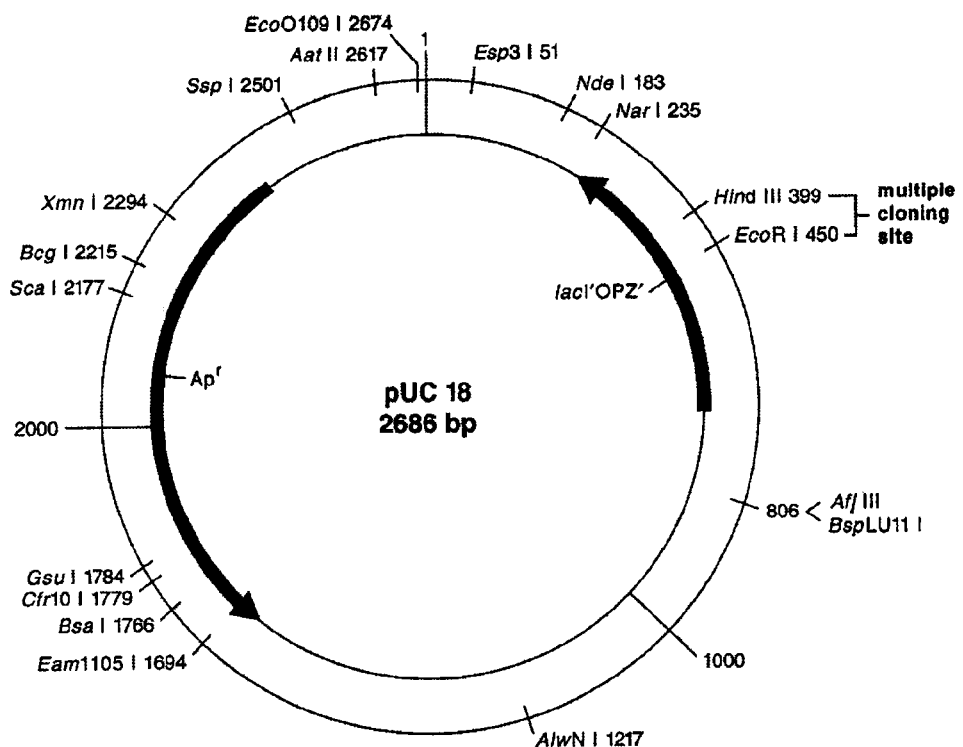
Figure 9:
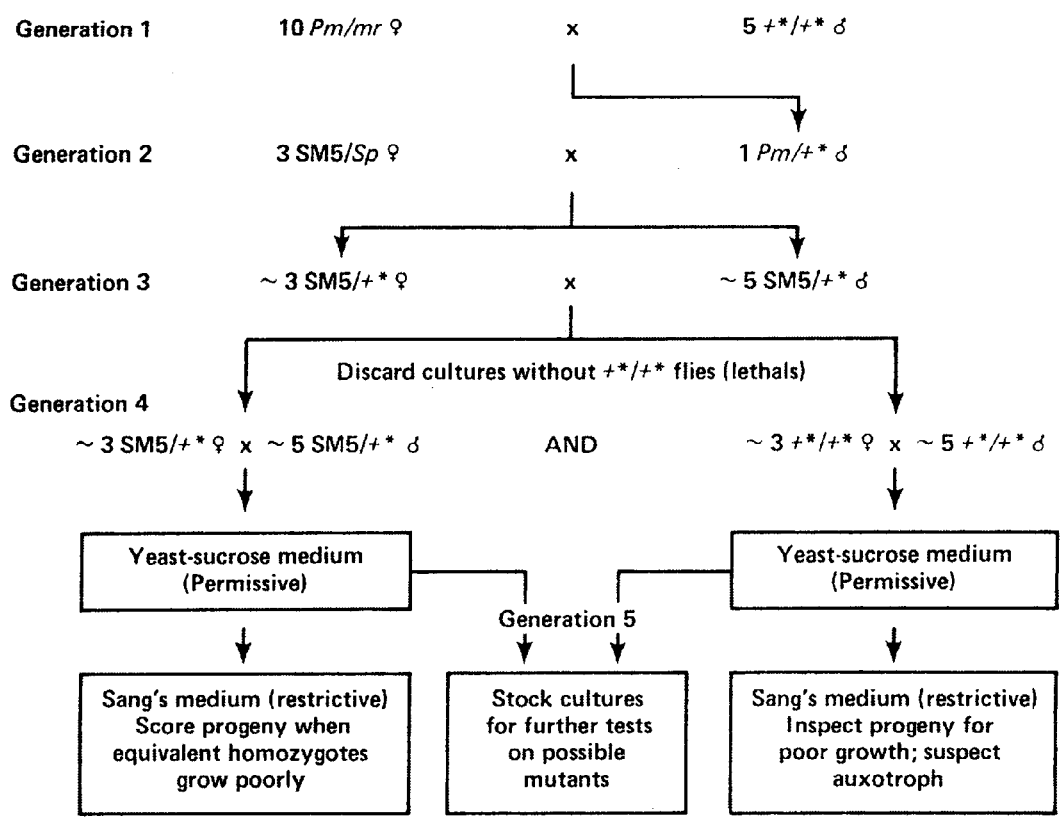
FIG. 9 is a protocol in the prior art used for the isolation of the second chromosomal auxotrophs. © 1985 Johnstone et al.
Figure 10:
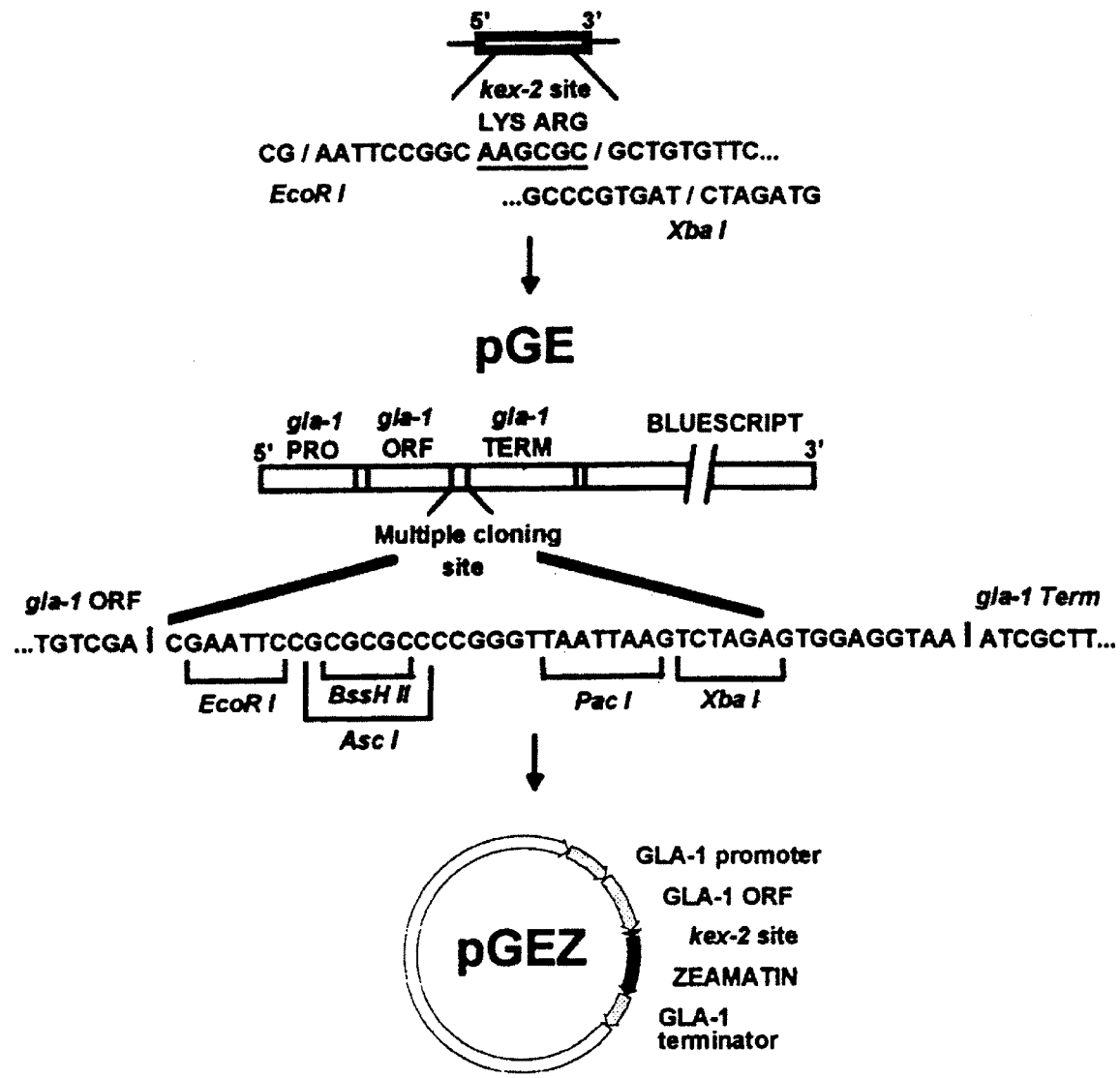
FIG. 10 is from the prior art showing a "schematic of the gla-1:zeamatin construct. PCR primers were designed to amplify the ORF of zeamatin-encoding cDNA by adding an EcoRI endonuclease site and a kex-2 protease site at the 5' end and an endonuclease site (XbaI site shown) at the 3' end after the first stop codon. The recombinant zeamatin-encoding cDNA fragment was ligated directionally into the multiple cloning site of pGE to form pGEZ for transformation into N. crassa. Sequences of pGE are illustrated with the permission of Neugenesis Corporation." © 1997 Rasmussen-Wilson et al.

The construction of the integration vector, pX, allowing the integration of the complete expression cassette at the amyE locus of the Bs chromosome (Shimotsu and Henner, 1986) is presented in FIG. 7. In addition, the nt sequence of the region between the promoter and the unique BamHI site which accepts foreign DNA is given. To facilitate the isolation of the complete xyl cassette a BglII site was introduced downstream of xylR allowing recovery of the complete cassette as a BglII-BamHI fragment (pLK04); this fragment can be inserted into any integration vector.

2.2. Cloning of the heat-shock genes grpE, dnaK, and dnaJ into pX and insertion at amyE To clone grpE, dnaK, and dnaJ into pX, the three genes were amplified by PCR using chromosomal DNA as template, and flanking BamHI sites were employed. All three plasmids, pX-grpE, pX-dnaK, and pX-dnaJ, produced functionally active proteins since they could complement appropriate Ec ts mutants for growth at the nonpermissive temperature (data not shown). Subsequently, the plasmids were transformed into Bs, and integrants were selected on LB plates containing Cm (5 μg/ml) resulting in the three strains, xyl-grpE, xyl-dnaK, and xyl-dnaJ. A straining carrying the original xyl expression cassette at amyE served as control." © 1996 Kim et al.

Similar methods are employed for the generation of eukaryotic recombinant host organisms expressing functional IMPDH enzyme. A *Neutrospora crassa* guanosine auxotroph is an appropriate fungal host organism. Coding regions of the human and *S. pyogenes* IMPDH are amplified by PCR and ligated into plasmid pGE (Neugenesis Corporation, Honolulu, Hi.)

"Bacterial strains and plasmids. *Escherichia coli* DH5α cells (Gibco BRL) were used in the subcloning, of plasmids according to procedures described by Sambrook et al. (22). Restriction enzymes were purchased from New England BioLabs and Promega and used according to the manufacturer's recommendations. Plasmid pMP6 contained a hygromycin resistance gene. Plasmid PZL1 contained the full-length zeamatin-encoding cDNA (Ciba-Geigy). Plasmid pGE with elements of the *N. crassa* GLA gene was obtained under license from Neugenesis Corporation (Honolulu, Hi.).

PCR site-directed mutagenesis. Plasmid PZLI containing the full-length zeamatin-encoding cDNA was used as the template DNA. Oligonucleotide primers were designed to integrate a 5' kex-2 site and restriction sites at both ends of the amplified zeamatin-encoding DNA fragment for chimeric cloning. A 655-bp DNA fragment was amplified with a forward primer containing the EcoRI and kex-2 sites (5'-GCGAATTCCGGCAAGCGCGCTGTGTTC-3') (SEQ ID NO: 10) and a reverse primer containing an XbaI site (5'-GTTCATCTAGATCACGGGCAGAAGACGA-3') (SEQ ID NO: 11).

Approximately 100 ng of template DNA was amplified in 50-μl reaction mixtures containing 100 μM deoxvnucleoside triphosphates, 0.6 μM (each) forward and reverse primers, 10 mM Tris-HCI (pH 8.3), 50 mM KCI. 2.0 mM mgcll, 10% (wt/vol) dimethvl sulfoxide, and 2.5 U of Taq DNA polymerase. Amplifications were performed in a GeneAmp 2400 thermal cycler (PerkinElmer) with an initial cycle of 94° C. for 3 min and 30 subsequent cycles of 94° C. for 1 min, 52° C. for I min, and 72° C. for 2 min. The amplification products were visualized on 1.0% (wt/vol) agarose gels in 1×TAE buffer (40 mM Tris-acetate, mM EDTA) stained with ethidium bromide.

Construction of the chimeric gla-1: zeaimiatin plasmid. The plasmid pGE, containing the gla-1 promoter, a truncated open reading frame (gla-1 ORF), a multiple cloning site, and the gla-1 terminator sequence, was used to form the chimeric gla-1:zeamatin construct (pGEZ). The gal-1 ORF was truncated at bp 376 of the GLA sequence reported by Stone et al. (25). The amplified zeamatin cDNA fragment and the plasmid pGE were digested with EcoRI and XbaI restriction enzymes and were isolated by agarose gel electrophoresis. The purified zeamatin DNA was ligated into pGE and transformed into *Escherichia coli* DH5α cells, and transformants were selected for ampicillin resistance as described in reference 22.

The nucleotide sequence of the resulting plasmid (PGEZ) was confirmed by restriction analyses and DNA sequencing from both ends of the gla-1:zeamatin construct. Primers were designed to sequence across the chimeric zeamatin cDNA from the flanking ends of the gla-1 ORF and gal-1 terminator. DNA sequencing was performed at Cornell University's DNA Services Facility (Ithaca, N.Y.)." © 1997 Rasmussen-Wilson et al.

The ligation products are transformed into an *N. crassa* guanosine auxotroph using the procedures described by Rasmussen-Wilson et al. (1997).

"Fungal strain and culture conditions. Wild-type *N. crassa* (74-OR8-1a), obtained from the Fungal Genetics Stock Center (Kansas City, Kans.), was grown on 5- and 50-ml 1.5% (wt/vol) agar-solidified cultures containing Vogel's medium N (3) and 1.% (wt/vol) sucrose. Cultures were grown for 5 to 7 days at 30° C. and stored at −20° C. Macroconidial suspensions were prepared by flooding 50-ml agar cultures with sterile water and filtering the resulting suspensions through sterile glass wool.

Cultures of *N. crassa* were grown in 250-ml baffled flasks containing 50 ml of Vogel's medium N supplemented with 0.6, 1.0 or 1.4% (wt/'Vol) glucose and 0.1% (vol/vol) Tween 20. Cultures were inoculated to $10^6$ cells/ml (final concentration) from frozen macroconidial stocks. The initial pH of the culture medium was 5.5. Cultures were incubated for 6 days at 25° C. on a rotary shaker at 100 rpm. Duplicate cultures were sampled every 12 h: 2 to 4 ml of culture fluid was cleared of particulates by using, 0.45-$\mu$m-pore-size syringe filters (MSI) and stored at −20° C. for subsequent analyses. Transformed *N. crassa* strains were grown similarly in 100-ml shaken cultures without Tween 20. Hyphae were harvested on day 4, and culture supernatants were collected by filtration through Whatman no. 1 filter paper and stored at −20° C. Culture supernatants were concentrated in pressure cells equipped with 10-kDa-cutoff filters (Amicon). Concentrated supernatants were filter sterilized with 0.45-$\mu$m-pore-size syringe filters prior to analysis.

Transformation of *N. crassa* with PGEZ.

Competent *N. crassa* cells were prepared according to a protocol described by Vollmer and Yanofsky (28) that was modified by Selitrennikoff and Sachs (23). Protoplasts were cotransformed with the gla-1:zeamatin construct (PGEZ) and pMP6 (to confer hygromycin resistance) at a ratio of 5 to 1 by a lipofectin-modified procedure described by Selitrennikoff and Sachs (23) Transformed conidia were germinated on plating medium containing 2% sorbose (3) and hygromycin (100 $\mu$g/ml).

Screening of transformed *N. crassa*. Primary transformants were transferred to agar slants containing Vogel's medium N with 1.5% (wt/vol) sucrose and hygromycin (200 $\mu$g/ml) and incubated at 25° C. for 5 to 7 days. Genomic DNA was extracted from primary transformants (8) and screened by PCR with primers specific for the gla-1 ORF-Zeamatin cDNA fusion. A 798-bp product was amplified with the forward gal-1p-specific primer (5'-GGAAGCTGAGGTTTGCCGAACTTAGACGACC-3') (SEQ ID NO: 8) and the zeamatin-specific reverse primer (5'-GAACTTGCACCCCGTGCGCGCCCAGATGC-3') (SEQ ID NO: 9). Amplifications were done in 10-$\mu$l reaction mixtures containing 100 ng of Genomic DNA, 200 $\mu$M deoxynucleoside triphosphates, primers (0.5 $\mu$M each). 50 mM Tris (pH 8.3), 250 $\mu$g of BSA/ml, 3.0 mM $MgCl_2$,. 10% (vol/vol) dimethyl sulfoxide, and 1.5 U of Taq DNA polymerase. PCR was performed on a Rapidcycler (Idaho Technology) with an initial cycle of 94° C. for 30 s and 30 subsequent cycles of 94° C. for 0 s, 50° C. for 0 s, and 72° C. for 15 s.

Isolation of homokaryons. Microconidium (homokaryon) induction and isolation were performed as described previously by Ebbole and Sachs (4). Microconidia were germinated at 34° C. on plating medium as described above for primary transformants. Colonies appearing after 3 to 7 days were transferred to agar slants containing hygromycin and Vogel's medium N with 1.5% (wt/vol) sucrose and hygromycin and. after 5 to 7 days of growth, were screened by PCR with zeamatin insert-specific primers." © 1997 Rasmussen-Wilson et al.

A suitable guanosine auxotroph is the gua-1 *N. crassa* strain characterized by Greer and Wellman (1980) and available from the Fungal Genetics Stock Center (Kansas City, Kans.). Expression of the IMPDH enzyme is induced by the addition of 1% glucose to the culture medium. The ability of the host organism to produce functional IMPDH is validated by growth of the recombinant host organism on Vogel's minimal medium (Davis and Serres, 1970) containing 1% glucose.

An appropriate insect host organism is a *Drosophila melanogaster* guanosine auxotroph. Coding regions of the human and *S. pyogenes* IMPDH are amplified by PCR and ligated into plasmid pPAC (Berkowith, et al., 1997)

"Drosophila Schneider SL2 cells were transfected by the calcium phosphate-DNA co-precipitation method (Graham and Van Der Eb, 1973) using a total of 3 $\mu$g of plasmid DNA (1.5 $\mu$g pTGFαLUC and 1.5 $\mu$g pPac vector) per dish. The Parental expression vector, pPac, and vectors containing the sense (pPAC-AP2+) and the antisense (pPAC-AP2-) AP2 cDNAs downstream of the Droophila actin 5C promoter were kindly provided by R. Buettner.

Plasmids

The effector vector $pP_{aC}$ was constructed by inserting a 3.8 kb EcoRI-SalI fragment of the P-element vector pUChsneo act(Bam) (Thummel et al., 1988) between the EcoRI and SalI sites of pUC18. The pUChsneo act(Bam) fragment is composed of a 2.7 kb act5C exon 1 proximal promoter fragment (−2.6 kb to 0.009 kb with respect to the transcription start site)and a 1.1 kb fragment containing the three act5C polyadenylation sequences, which was the site used to insert the protein coding sequences. Transcripts produced from effector plasmids with intron-containing inserts are spliced in Schneider line 2 cells (Winslow et al., 1989), but introns are not necessary for expression as most cDNA inserts also yield the expected RNAs and proteins." © 1997 Berkowith et al.

and the ligation products are used to transform a D. melanogaster guanosine auxotroph using a lipofection reagent (e.g., CellFECTIN™, Life Technologies, Gaithersburg, Md.). A suitable guanosine auxotroph is the burgua2- 1 strain characterized by Johnstone et al. (1985).

"Isolation and Description of the Mutants

Ade2-1 and ade3-1 were isolated after ethyl methanesulfonate treatment of wild-type male parents (from the "Amherst inbred" line) using the genetic screen described by Naguib and Nash (1976). This screen also produced a black (b: 2-48.5)-bearing chromosome in which $bur^{gua2-1}$ was later induced using the same method. $bur^{gua2-1}$ was originally called guanosine2-1 (gua2-1) but was renamed in accord with the results of complementation test presented later.

The Nutritional Phenotypes

The mutants were initially isolated on the basis of their reduced viability on Sang's nucleoside -free medium compared to permissive medium (yeast sucrose) and then characterized with respect to their response on Sang's medium supplemented with 4.0 mg/ml RNA. The mutations were kept heterozygous with SM5, a balancer chromosome. $Bur^{gua2-1}$ homozygotes are completely inviable on restrictive medium and are 40% supported on RNA-supplemented Sang's medium.

Table 4 shows the results of rearing each of the auxotrophs under a variety of supplemental conditions.

Table 4. Growth Characteristics of ade2-1, ade3-1, and $bur^{gua2-1}$ on Sang's Medium Supplemented with Bases and Nucleosides$^a$

TABLE 4

Growth Characteristics of ade2-1, ade3-1, and $bur^{gua2-1}$ on Sang's Medium Supplemented with Bases and Nucleosides$^a$

| | Mutant | | | | | |
|---|---|---|---|---|---|---|
| | ade2-1 | | ade3-1 | | $bur^{gua2-1}$ | |
| Supplement | Survivors | Delay | Survivors | Delay | Survivors | Delay |
| Adenosine | 288/352 | 0.1 | 306/455 | −0.3 | 0/251 | — |
| Inosine | 250 | 0 | 253/300 | 1.0 | 2/212 | 4.1 |
| Guanosine | 6/213 | 5.1 | 39/362 | 6.6 | 350/290 | 0.1 |
| Uridine | 0/311 | — | 0/229 | — | 0/519 | — |
| Cytidine | 0/288 | — | 139/524 | 7.3 | 0/232 | — |
| Adenine | 77/177 | 1.6 | 181/273 | 0.6 | 3/209 | 6.8 |
| Hypoxanthine | 0/199 | — | 176/473 | 7.6 | 0/131 | — |
| Guanine | 0/385 | — | 40/849 | 5.4 | 0/322 | — |
| Uracil | 0/253 | — | 31/549 | 7.8 | 0/96 | — |
| Cytosine | 0/214 | — | 27/707 | 6.8 | 0/150 | — |
| Allopurinol | ND | | ND | | 0/151 | — |
| 1 mM guanosine | ND | | ND | | 6/226 | — |
| Allopunnol + 1 mM guanosine | ND | | ND | | 61/72 | 1.9 |
| Allopurinol + guanine (3.2 mM) | ND | | ND | | 0/96 | — |

Results from ade2-1 and ade3-1 were determined in five crosses of five homozygous E and five heterozygous G. The recprocal cross was used with $bur^{gua2-1}$. In all cases, five replicate crosses were set. Data are represented as in Table I. Nucleoside and bases were present at a concentration of 3.2 mM unless noted otherwise. Allopurinol was added at 1 mM, at which concentration it is somewhat toxic (Nash, unpublished).
ND indicates that an experiment was not performed." © 1985 Johnstone et al.

Transformed cells are maintained in Schneider's Medium (Life Technologies), 10% fetal bovine serium, 0.1 mM nonessential amino acids, and 50 μg/ml gentamicin. The ability of the host organism to produce functional IMPDH is validated by growth of the recombinant host organism in Schneider's medium lacking which lacks a source of guanine nucleotides.

Example 2

Selective Growth of Recombinant IMPDH Host Organisms

Four H712 clones (plate areas with clones designated H1 to H4) containing a recombinant expression vector for human IMPDH and two H712 clones containing a recombinant expression vector for S. pyogenes IMPDH (plate areas with clones designated S1 and S2) were spread on culture plates containing ampicillin and minimal nutrients for cell growth. The growth medium consisted of M9 minimal agar media (Perbal, 1984) supplemented with thiamin, tyrosine, histidine, glutamine, and tryptophan. The clones were simultaneously streaked on minimal nutrient plates containing guanosine (30 μg/ml), IPTG (50 μg/ml) or IPTG plus MPA (50 μg/m, a human, but not bacterial, IMPDH inhibitor). Plates were incubated at 37° C. overnight and bacterial growth assessed by visual inspection. Table 5 illustrates growth specificity of H712 clones expressing human (designated H1, H2, H3 and H4) or S. pyogesies (designated S1 and S2) IMPDH.

TABLE 5

Growth Specificity of H712 Clones Expressing human (H1, H2, H3, and 1–14) and S. pyogenes (SI and S2) IMPDH.

| Plate | H712 Clone | | | | | |
|---|---|---|---|---|---|---|
| Additions | H1 | H2 | H3 | H4 | S1 | S2 |
| None (Control) | – | – | – | – | – | – |
| Guanosine (30 µg/ml) | + | + | + | + | + | + |
| IPTG (50 µg/ml) | + | + | + | + | + | + |
| IPTG + MPA (50 µg/ml) | – | – | – | – | + | + |

+ = Bacterial growth
– = No growth

No growth was observed on the plate containing minimal media (without any additional components) confirming the auxotrophic phenotype and demonstrating the inability of the expression system to produce sufficient IMPDH in the absence of inducer to permit bacterial growth. Bacterial growth was observed on the plate containing guanosine confirming the observation that the H712 strain is defective in purine nucleotide synthesis. In conjunction with the previous controls, the growth on the plate containing IPTG indicated the ability of the induced product to compensate for the IMPDH deficiency in [1712. This ability is attributable to the expression of the human or Streptococcal IMPDH enzymes. To establish that the growth is attributable to specific induction of IMPDH expression from the pJF118EH expression plasmid, the expression clones were streaked on a minimal plate containing IPTG and mycophenolic acid (MPA). MPA is an effective inhibitor of human IMPDH but does not effectively inhibit IMPDH from S. pyogenes. On this plate, growth was only observed in plate areas S1 and S2 corresponding to bacterial clones that are expressing S. pyogenes IMPDH. These observations indicate the bacterial growth profile is attributable to the specific expression of either the human or S. pyogenes IMPDH enzymes.

Example 3

Dose Dependent Inhibition of Recombinant Host Growth

Figure 2:
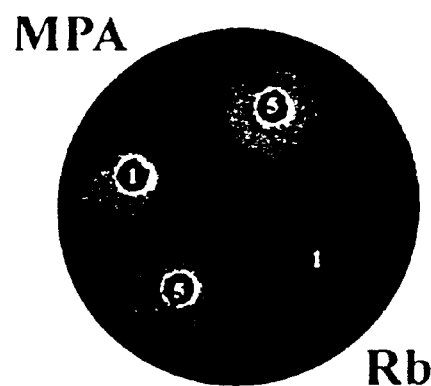
FIG. 2 illustrates assays of candidate inhibitors.
Figure 2:
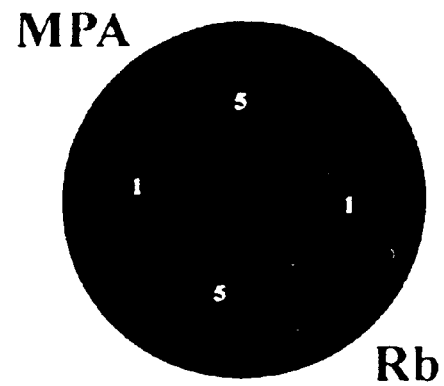
Figure 2:
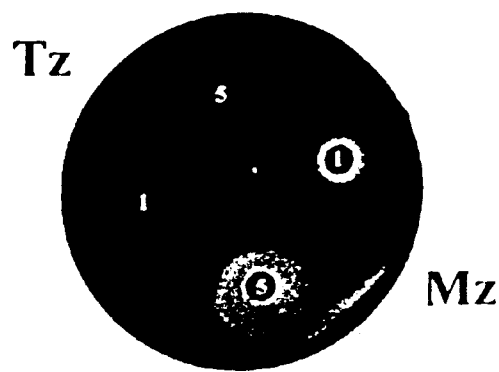
Figure 2:
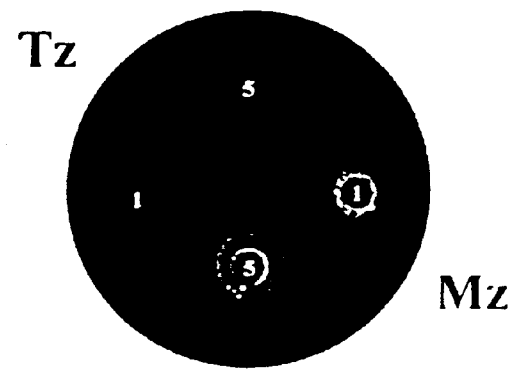

To illustrate the practicality of screening for inhibitors using the invention, the indicated amounts of MPA (noted on FIG. 2 in µg) were added to 7 mm filter disks and the disks were placed on a lawn of H712 bacteria containing the human IMPDH expression plasmid. MPA is known to be an effective inhibitor of the human IMPDH enzyme. A control disk containing the solvent but no inhibitor was placed in the center of the dish. The growth medium consisted of M9 minimal agar supplemented with thiamin, tyrosine, histidine, glutamine, and tryptophan and IPTG. The plate medium also contained IPTG for induction of enzyme expression. The dose dependent inhibition of bacterial growth illustrates the ability of this method to provide a quantitative indication of the level of inhibition and demonstrates the utility for application of this invention to a variety of screening procedures.

Example 4

Assays of Candidate Inhibitors

Figure 3:
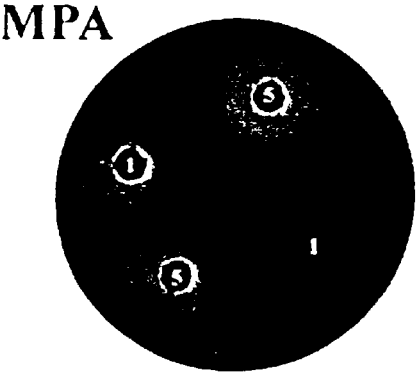
FIG. 3 illustrates reduction of growth inhibition by guanosine.
Figure 3:
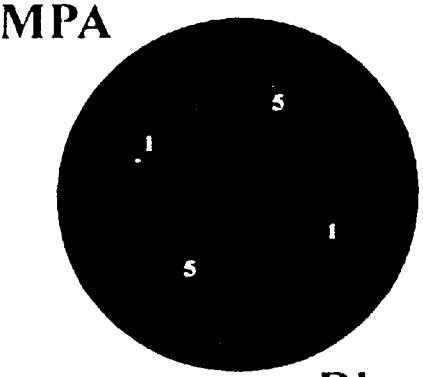

To further illustrate the practicality of screening for inhibitors using the invention, various amounts of several different IMPDH inhibitors were added to 7 mm filter disks and the disks placed on a lawn of H712 bacteria containing either the human or S. pyogenes IMPDH expression plasmid and IPTG for induction of enzyme expression. These inhibitors were selected on the basis of reports in the literature regarding specificity for inhibition of human IMPDH. Both MPA and Rb are clinically useful and MPA is known to inhibit human, but not bacterial IMPDH (Hupe el 1986). The remaining inhibitors, Rb, Tz, and Mz, require cellular activation for utility as IMPDH inhibitors. These inhibitors are known to inhibit human IMPDH but their effect on bacterial IMPDH enzymes has not been investigated. The inhibitor disks were placed on a lawn of H712 bacteria containing either the human or S. pyogenes IMPDH expression plasmid and IPTG for the induction of enzyme expression, as indicated by a clear zone of growth inhibition. A control disk containing the solvent but no inhibitor was placed in the center of the dish. The growth medium consisted of M9 minimal agar supplemented with thiamin, tyrosine, histidine, glutamine, and tryptophan and IPTG. After iincubation at 37° C. overnight, the plates were examined for inhibition of bacterial cell growth. For several of the inhibitors, a clear area was observed around the filters corresponding to the degree of growth inhibition. (FIG. 3) Various inhibition patterns were observed for bacteria containing the human or S. pyogenes IMPDH expression vectors that ranged from no inhibition, to inhibition of human IMPDH, to inhibition of both forms of IMPDH. Furthermore all of the growth inhibitory chemicals showed a differential between the low and high does. The inhibition profiles obtained with this panel of IMPDH inhibitors demonstrate the IMPDH enzyme produced in bacteria retains the biochemical and kinetic characteristics of the source (i.e. human or S. pyogenes). The results also illustrate the utility of this approach for identification of the inhibitory spectrum of IMPDH inhibitors.

This example illustrates the ability of this invention to identify clinically useful features of the potential IMPDH inhibitors. Clinically useful agents must be transported into the target organism and may require activation for therapeutic effectiveness. In this screening procedure, the use of a host organism that mimics the characteristics of the eventual therapeutic target can provide useful information regarding clinically useful properties of potential therapeutic agents. The results demonstrate Rb and Mz are transported into the bacterial cells and are activated by the host system to a form, which is capable of inhibiting IMPDH. Thus, this method inherently excludes compounds that might be impermeable to the host organism. Alternatively, because many inhibitory compounds require activation by chemical modification, this method can be applied to determine the competency of a host organism for metabolic activation of IMPDH inhibitors.

Example 5

Guanosine Reduction of Growth Inhibition Due to Inhibition of IMPDH

Figure 4:
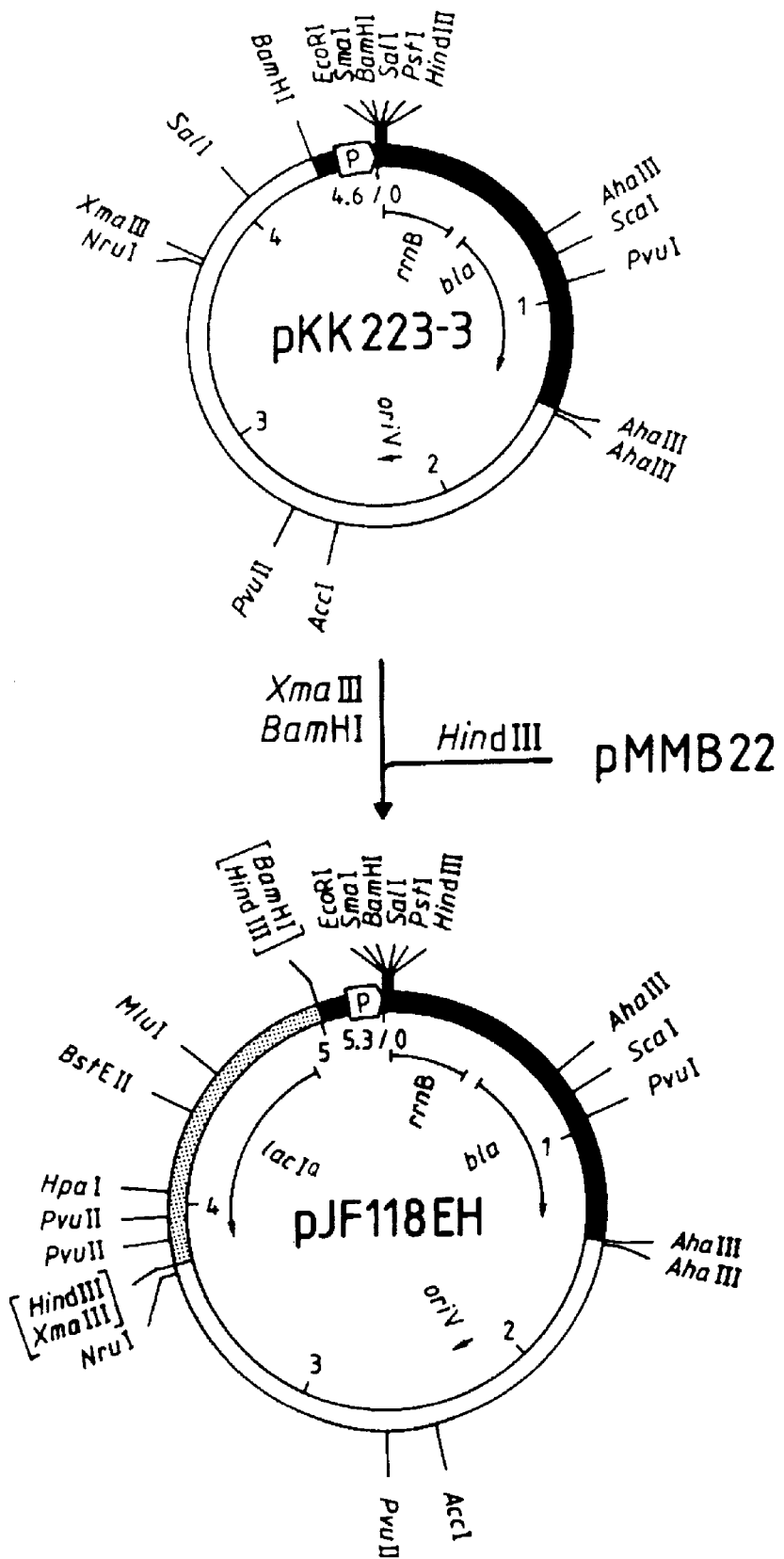
FIG. 4 is a map in the prior art of plasmid pJF118EH showing; "construction of the autoregulated expression vector plasmids. A 1247-bpHindIII fragment (shaded area) from pMMB22 (Bagdasarian et al., 1983) containing the lacI$^Q$ gene was inserted into pKK233-3 between the restriction sites XmaI (bp 3771) and BamHI (bp 4318), resulting in pJF118EH." © 1986 Fürste et al.
Figure 5:
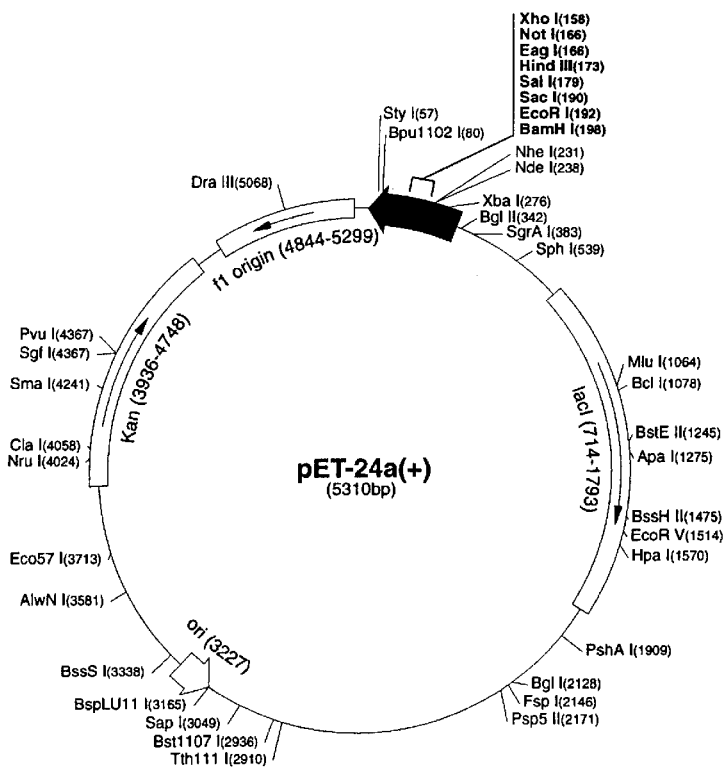
FIG. 5 is a map in the prior are of plasmid pET-24a(+). © 1995 Hager et al.
Figure 6:
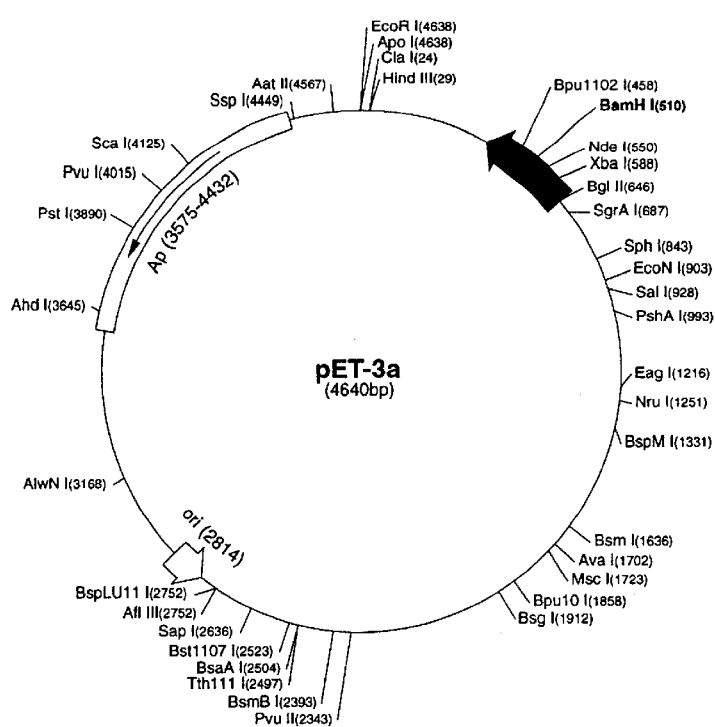
FIG. 6 is a map in the prior art of plasmid rET-3a. © 1994 Dayton et al.

To demonstrate that the observed growth inhibition in Example 4 was specific for IMPDH, some of the inhibitor filter disks were placed on a lawn of H712 bacteria on plated supplemented with guanosine. The indicated amounts of MPA (noted on the filter, in µg) were added to 7 mm filter disks and the disks placed on a lawn of H712 bacteria containing the human IMPDH expression plasmid. The growth medium consisted of M9 minimal agar supplemented with thiamin, tyrosine, histidine, glutamine, and tryptophan and IPTG with one of the plates containing 50 μg/ml of guancsine. After incubation at 37° C. overnight, the plates were examined for inhibition of bacterial cell growth. The restoration of bacterial growth on the plates containing exogenous guanosine (FIG. 4) indicates the specificity of this chemical for IMPDH. On these plates, the exogenous guanosine reduced the inhibitory effect of the mycophenolic acid. The ability of guanosine to ameliorate the growth inhibition indicates the specificity of these chemicals for IMPDH.

DOCUMENTS CITED

Allison, A. C., et al, Punne metbolism and immunosuppressive effects of mycophenclate mofeti]. *Clin. Transplant.* 10(1):77–84 (1996).

Bagdasarian M. M., et al. Activity of the hybrid trp-lac (tac) promoter of *Escherichia coli* in *Pseudomonas putida*. Constnuction of broad-host-range, controlled-expression vectors. *Gene.* 26(2–3):273–82 (1986).

Berkowitz, E. A., et al, Transcription factor AP2 is required for expression of the rat transfonning growth factor-α gene. *Oncogene* 14. (1997).

Collart, F. R., et al. Cloning characterization and sequence comparison of the gene coding for IMP dehydrogenase from *Pyrococcus furiosus. Gene* 174(2):209–216 (1996).

Conrad, B., et al. A T7 promoter, specific inducible protein expression system for *Bacillus subtilis. Mol Gen. Genet,* 250:230–236 (1996).

Davis, R. H. and de Serres, F. J. Genetic azd microbiological reserach techniques for *Neurospora crassa. Methods Enzymol,* 17A:79–143 (1970).

Dayton J S, et al Related Articles Effects of human T lymphocyte activation on inosine monophosphate dehydrogenase expression. *J Immunol.* 152(3):984–91 (1994).

Freese E., et al Partial putine deprivation causes sporulnation of *Bacillus subtilis* in the presence of excess ammonia, glucose and phosphate, *J Gen. Microbiol.* 115(1):195–205 (1979).

Fürste, J. P., et al Molecular cloning of the plasmid RP4 primase region in a multi-host-range tacP expression vector. *Gene* 48:119–131 (1986).

Gillespie, S. H., et al. The biological cost of antimicrobial resistance. *Trends Microbiol,* 5(9):337–339 (1997).

Greer, W. L. and Weliman, A. M. Isolation and characterization of guanine auxotrophs in *Neurospora crassa. Can, J. Microbiol.* 26(12);1412–1415 (1980).

Hager, P. W., et al. Recombinant human inosine monophosphate dehydrogenase type I and type II proteins. Purification and characterization of inhibitor binding. *Biochem. Pharmacol* 49(9):1323–1329 (1995).

Halloran, P. F, Molecular mechanisms of new immunosuppressants. *Clin, Transplant.* 10(1): 118–123 (1996).

Huete-Perez, J. A., et al Identification of the IMP binding site in the IMP dehydrogenase from *Tritrichomonas foetus. Biochemistry* 34(42):3889–13894 (1995).

Hughes, J., et a. New immunosupressive drugs in organ transplantation. *Clin. Pharmacol* 36(12):1081–1092 (1996).

Huggins, J. W., et al. Prospective double-blind concirent, placebo controlled clincal trials of intravenous ribavirin therapy of hemorrhagic fever with renal syndrome. *J. Infect. Dis.* 164:1119–1127 (1991).

Hupe, D. J., et al. IMP dehydrogenose from the intracellular parasitic protozoan *Eimeria tenella* and its inhibition by mycophenolic acid, *J. Biol. Chem.* 261(18):8363–8369 (1986).

Huynh, T. V., et al. *DNA Cloning* 1:49–88 (1985).

Japour, A. J., et al. A phase-I study of the safety, pharmacokinetics, and antiviral activity of combination didanosine and ribavirin in patients with HIV-1 disease. AIDS Clinical Trials Group 231 Protocol Team. *J. Acquir. Immune. Defic. Syndr. Hm. Retrovirol.* 13(3):235–246 (1996).

Jayaram, et al. Clinical pharmacokinetic study of tiazofurin administered as a 1-hour infusion. *Int. J. Cancer.* 51 (2):182–188 (1992).

Johnstone, M. E. et al. Three purine auxotrophic loci on the second chromosome of *Drosophila melanogaser. Biochem. Genet.* 23:539–555 (1985).

Karmazyn-Campbelli C, et al The spoIIN279(ts) mutation affect the FtsA protein of *Bacillus subtilis. Biochimie.* (7–8):689–94 (1992).

Kim, L., et al. A xylose-inducible *Bacillus subtilis* integration vector and its application. *Gene* 181:71–76 (1996).

Klepser, M. E. Update on antifungal xesistance. *Trends Microbiol.* 5(9):372–375 (1997).

Maniatis, T., et al. Molecular Cloning, A Laboratory Manual (1982).

Miyagawa, K., et al, Cloning of the *Bacillus subtifis* IMP dehydrogenase gene and its application to incneased production of guanosine. *Biotechnology* 4:225–228 (1986).

Mortensen, R. Overview of Gene Targeting by Homologous Recombination in Current Protocols in Molecular Biology, pp. 915.1–9.15.6 (1993, F. M., Ausubel et al., eds,).

Nijkamp, H. J. J. and De Hann, P. G. Genetic and Biochemical studies of the guanosine 5'-monophosphate pathway in *Escherichia coli, Biochim Biophys Acta* 145:31–40 (1967).

Perbal, B. A Practical Guide to Molecular Cloning (1984).

Rasmussen-Wilson, S. J., et al. Expression of a plant protein by *Neurospora crassa. Appl. Environ. Microbiol* 63(9):3488–3493 (1997).

Roth, M. G. Protein Expression in Animal Cells in Methods in Cell Biology, pp. 1–379 (Academic Press, San Diego, 1994)

Rygas T and Hillen, W. Inducible high-level expression of heterologous genes in *Bacillus megaterium* using the regulatory elements of the xylose-utilization operon. *Appl Microbiol Biotechnol.* 35(5):594–9 (1991).

Smith, D. W. et al. A controlled trial of aerosolized ribavirin in infants receiving mechanical ventilation for severe respiratory syncytial virus infection. *N. Engl J. Med.* 325(1):24–29 (1991).

Stong-Gunderson, J. M. and Palumbo, A. V. Alternative method for rapidly screenlng microbial isolates for their potential to degrade volatile contaminants. *J. Ind. Microbiol.* 13(6):361–366 (1994).

Tiedeman, A. A. and Smith, J. M. Isolation and sequence of a cDNA encoding mouse IMP dehydrogenase *Gene* 97:289–293 (1991).

Wang, W., et al. Inactivation of inosine 5'-monophosphate dehydrogenase by the antiviral agent 5-ethynyl-1-beta-D-ribafuranosylimidazole-4-carboxamide 5'-monophosphate. *Biochemistry* 35(1):95–101 (1996).

Winans, S. C., et al, Site directed insertion and deletion mutagenesis with cloned fragments in *Escherichia coli, J. Bacteriol.* 161:1219–1221(1985).

What is claimed is:

1. A method for identifying an inhibitor of IMPDH from a candidate inhibitor, said method comprising:
   (a) obtaining a recombinant auxotrophic strain that does not express a native IMPDH enzyme and expresses an IMPDH from another species in its cells;
   (b) applying the candidate inhibitor to cells of the strain; and
   (c) determining whether the candidate agent is an inhibitor of IMPDH.

2. The method of claim 1, wherein the strain is bacterial.

3. The method of claim 2, wherein the strain is an *Escherichia coli* strain.

4. The method of claim 3, wherein the *Escherichia coli* strain is designated H712.

5. The method of claim 2, wherein the strain is a *Bacillus subtilus* strain.

6. The method of claim 1, wherein the strain is eukaryotic.

7. The method of claim 6, wherein the eukaryotic strain is Neurospora.

8. The method of claim 6, wherein the strain is an insect strain.

9. The method of claim 1, wherein the IMPDH expressed from another species is from the species *Homo sapiens*.

10. The method of claim 1, wherein the IMPDH expressed from another species is from a bacterial species.

11. The method of claim 10, wherein the bacterial species is *Streptococcus pyogenes*.

12. The method of claim 1, wherein expression of IMPDH is induced.

13. The method of claim 12, wherein expression is induced by IPTG.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

GTACAAAGCT TCATATGGCC GACTACCTGA TTAGTGGGGG CACG                44

(2) INFORMATION FOR SEQ ID NO:2:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

TGACAAAGCT TAGATCTTCA GAAAAGCCGC TTCTCATACG AA                  42

(2) INFORMATION FOR SEQ ID NO:3:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

GTACAAAGCT TCATATGGCG GACTACCTGA TCAGCGGCGG CACC                44

(2) INFORMATION FOR SEQ ID NO:4:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TGACAAAGCT TAGATCTTCA GTACAGCCGC TTTTCGTAAG AG                  42

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
CAGATGGATC GCCTTCGCAG                                                  20
```

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

```
CTGTGGACCA CTCAGTTATG                                                  20
```

(2) INFORMATION FOR SEQ ID NO:7:

(i) SEQUENCE CHARACTERISTICS:
        (A) LENGTH: 173 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
AACATTGAAA TAAACATTTA TTTTGTATAT GATGAGATAA GTTAGTTTAT TGGATAACAA       60

ACTAACTCAA TTAAGATAGT TGATGGATAA ACTTGTTCAC TTAAATCAAA GGGGAAATG       120

ACAAATGGTC CAAACTGTGA TATCTAAAAA TCAAGGGGA AATGGGATCC TCT              173
```

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
GGAAGCTGAG GTTTGCCGAA CTTAGACGAC C                                     31
```

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
GAACTTGCAC CCCGTGCGCG CCCAGATGC                                        29
```

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
GCGAATTCCG GCAAGCGCGC TGTGTTC                                                    27

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GTTCATCTAG ATCACGGGCA GAAGACGA                                                   28

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

CGAATTCCGG CAAGCGCGCT GTGTTC                                                     26

(2) INFORMATION FOR SEQ ID NO:13:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GCCCGTGATC TAGATG                                                                16

(2) INFORMATION FOR SEQ ID NO:14:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

TGTCGACGAA TTCCGCGCGC CCCGGGTTAA TTAAGTCTAG AGTGGAGGTA AATCGCTT          58
```